(12) United States Patent
Nathan et al.

(10) Patent No.: US 9,700,525 B2
(45) Date of Patent: Jul. 11, 2017

(54) CONTINUOUS LOCAL SLOW-RELEASE OF THERAPEUTICS FOR HEAD AND NECK PROBLEMS AND UPPER AERODIGESTIVE DISORDERS

(71) Applicant: Board of Supervisors of Louisiana State University and Agricultural and Mechanical College, Baton Rouge, LA (US)

(72) Inventors: Cherie Ann Nathan, Shreveport, LA (US); James Douglas Boudreaux, Shreveport, LA (US)

(73) Assignee: Board of Supervisors of Louisiana State University and Agricultural & Mechanical College, Baton Rouge, LA (US)

( * ) Notice: Subject to any disclaimer, the term of this patent is extended or adjusted under 35 U.S.C. 154(b) by 0 days.

(21) Appl. No.: 14/796,557

(22) Filed: Jul. 10, 2015

(65) Prior Publication Data
US 2016/0051492 A1 Feb. 25, 2016

Related U.S. Application Data

(63) Continuation of application No. 12/544,997, filed on Aug. 20, 2009, now abandoned.

(60) Provisional application No. 61/189,563, filed on Aug. 20, 2008.

(51) Int. Cl.
| | |
|---|---|
| *A61K 31/12* | (2006.01) |
| *A61K 31/353* | (2006.01) |
| *A61K 45/06* | (2006.01) |
| *A61K 9/58* | (2006.01) |
| *A61K 9/68* | (2006.01) |

(52) U.S. Cl.
CPC ............ *A61K 31/12* (2013.01); *A61K 9/0058* (2013.01); *A61K 31/353* (2013.01); *A61K 45/06* (2013.01)

(58) Field of Classification Search
CPC .... A61K 2300/00; A61K 33/42; A61K 31/13; A61K 31/465; A61K 45/06; A61K 31/12; A61K 9/0056; A61K 31/05; A61K 9/0058; A61K 31/404; A61K 31/455; A61K 36/48; A61K 9/146; A61K 31/405; A61K 8/347
See application file for complete search history.

(56) References Cited

U.S. PATENT DOCUMENTS

| | | | |
|---|---|---|---|
| 4,400,372 A | * | 8/1983 | Muhler .................... A61K 8/24 424/48 |
| 5,145,684 A | | 9/1992 | Liversidge et al. |
| 5,549,906 A | | 8/1996 | Santus |
| 5,626,838 A | | 5/1997 | Cavanaugh, Jr. |
| 5,861,415 A | | 1/1999 | Majeed et al. |
| 6,280,761 B1 | | 8/2001 | Santus |
| 6,300,343 B1 | | 10/2001 | Steiner |
| 6,486,203 B1 | * | 11/2002 | Dannenberg .......... A61K 9/0056 514/403 |
| 6,716,883 B1 | * | 4/2004 | Casper .................... A61K 8/347 514/733 |
| 2003/0084912 A1 | | 5/2003 | Pera |
| 2004/0076665 A1 | | 4/2004 | Graff et al. |
| 2004/0194793 A1 | | 10/2004 | Lindell et al. |
| 2005/0049299 A1 | * | 3/2005 | Aggarwal .............. A61K 45/06 514/456 |
| 2006/0264497 A1 | * | 11/2006 | Zeligs .................... A61K 8/492 514/414 |
| 2008/0076821 A1 | | 3/2008 | Di Mauro |
| 2008/0107749 A1 | * | 5/2008 | Maitra .................... B01J 13/14 424/501 |
| 2012/0052095 A1 | | 3/2012 | Chaniyilparampu et al. |
| 2013/0029905 A1 | | 1/2013 | Madhavamenon et al. |

FOREIGN PATENT DOCUMENTS

| | | |
|---|---|---|
| EP | 1 837 030 A1 | 9/2007 |
| WO | WO-2007/103435 | 9/2007 |

OTHER PUBLICATIONS

Sharma et al. "Phase I Clinical Trial of Oral Curcumin: Biomarkers of Systemic Activity and Compliance", Clinical Cancer Research, vol. 10, Oct. 15, 2014, pp. 6847-6854.*
U.S. Appl. No. 14/602,178, filed Jan. 21, 2015, LSU Research & Technology Foundation.
Aggarwal et al., Targeting inflammatory pathways for prevention and therapy of cancer: short-term friend, long-term foe:, Clin Cancer Res, 2009, 15:425-30.
Anand et al., "Cancer is a preventable disease that requires major lifestyle changes", Pharm Res, 2008, 25:2097-116.
Anand, P, "Bioavailability of Curcumin: Problems and Promises", Mol Pharmaceutics, 2007, 4:807-18.
Begum, An et al. "Curcumin Structure-Function, Bioavailability, and Efficacy in Models of Neuroinflammation and Alzheimer's Disease." The Journal of Pharmacology and Experimental Therapeutics 2008;326(1):196-208.

(Continued)

*Primary Examiner* — Audrea Buckley
(74) *Attorney, Agent, or Firm* — Foley & Lardner LLP (57) ABSTRACT

The invention features formulations for the local delivery of therapeutically effective doses of curcumin to treat head and neck disorders and upper aerodigestive disorders. Also disclosed are use of the formulations for delivery of other phytochemicals, or the combination of phytochemicals for the treatment of said disorders. Furthermore, these formulations can be used to deliver the recommended daily allowance of vitamins and/or minerals to children or adults.

8 Claims, 3 Drawing Sheets

(56) References Cited

OTHER PUBLICATIONS

Benner et al., "Prevention of second primary tumors with isotretinoin in patients with squamous cell carcinoma of the head and neck: long-term follow-up", J Natl Cancer Inst., 1994, 86(2):140-1.
Bisht et al., "Systemic delivery of curcumin: 21st century solutions for an ancient conundrum", Current Drug Discoveries Technology, 2009, 6(3):192-9.
Bisht, S et al. "Polymeric nanoparticle-encapsulated curcumin ("nanocurcumin"): a novel strategy for human cancer therapy." Journal of Nanobiotechnology 2007,5:3:1-18.
Carroll et al., "Phase IIa clinical trial of curcumin for the prevention of colorectal neoplasia", Cancer Prev Res, 2011, 4(3):354-64.
Dhillon, et al., "Phase II Trial of Curcumin in Patients with Advanced Pancreatic Cancer", Clin Cancer Res., 2008, 14(14):4491-9.
Dhooge et al., "Multiple primary malignant tumors in patients with head and neck cancer: results of a prospective study and future perspectives", Laryngoscope, 1998, 108(2):250-6.
Garcea, et al., "Consumption of the putative chemopreventative agent curcumin by cancer patients: assessment of curcumin levels in the colorectum and their pharmacodynamics consequences", Cancer Epidemiol Biomarkers Prev, 2005, 14:120-25.
Garcea, et al., "Detection of curcumin and its metabolites in hepatic tissue and portal blood of patients following oral administration", Br J Cancer, 2004, 90:1011-15.
Gescher et al., "Cancer chemoprevention by dietary constituents: a tale of failure and promise", The Lancet Oncol, 2001, 2:371-9.
Hong et al., "13-cis-retinoic acid in the treatment of oral leukoplakia", N. Engl J Med., 1986, 315(24):1501-5.
Hong et al., "Curcumin inhibits tyrosine kinase activity of p185neu and also depletes p185neu1", Clin Cancer Res., 1999, 5(7):1884-91.
Hong et al., "Prevention of second primary tumors with isotretinoin in squamous-cell carcinoma of the head and neck", New England Journal of Medicine, 1990, 323(12):795-801.
Huang, M et al. "Inhibitory effect of curcumin, chlorogenic acid, caffeic acid, and ferulic acid on tumor promotion in mouse skin by 12-O-tetradecanoylphorbol-13-acetate." Cancer Res 1988,48(21):5941-6.
Huang, MT et al. "Inhibitory effects of curcumin on tumor initiation by benzo[a]pyrene and 7,12-dimethylbez[a]anthracene." Carcinogenesis, Nov. 1992:13(11):2183-6. (Abstract).
Ireson, et al., "Metabolism of the cancer chemopreventative agent curcumin in human and rat intestine", Cancer Epidemiol. Biomarkers Prev, 2002, 11:105-11.
Lao et al., "Dose escalation of a curcuminoid formulation", BMC Complement Altern Med, 2006, 6:10.
Li, M et al. "Curcumin, a dietary component, has anticancer, chemosensitization, and radiosensitization effects by down-regulating the MDM2 oncogene through the PI3K/mTOR/ETS2 pathway." Cancer Res 2007,67(5):1988-96.
Li, N et al. "Inhibition of 7,12-dimethylbenz[a]anthracene (DMBA)-induced oral carcinogenesis in hamsters by tea and curcumin." Carcinogenesis 2002,23(8):1307-13.
Lippman et al., "Cancer chemoprevention", Journal of Clinical Oncology, 1994, 12(4):851-73.
Lippman et al., "Second malignant tumors in head and neck squamous cell carcinoma: the overshadowing threat for patients with early-stage disease", Int J Radiat Oncol Biol Phys., 1989, 17(3):691-4.
Marczylo, TH et al. "Comparison of systemic availability of curcumin with that of curcumin formulated with phospatidycholine." Cancer Chemother Pharmacol, 2007;60:171-177.
Nathan, C et al., "An exploratory biomarker trial of an mTOR inhibitor in subjects with newly diagnosed advanced stage HNSCC", Proceedings AACR Supplement, 2007, 48:42.
Nathan, C et al. "Expression of eIF4E during head and neck tumorigenesis: possible role in angiogenesis." Laryngoscope 1999,109(8):1253-8.
National Institute of Health, "Head and Neck Cancers", 2013 retrieved Sep. 30, 2013, from National Cancer Institute: http://www.cancer.gov/cancertopics/types/head-and-neck/head-neck-fact-sheet.
Park et al., "Molecular changes in the multistage pathogenesis of head and neck cancer", Cancer Biomark., 2010, 9(1-6):325-39.
Rao et al., "NSAIDs and chemoprevention", Curr Cancer Drug Targets, 2004, 4(1):29-42.
Sharma et al. "Phase I Clinical Trial of Oral Curcumin: Biomarkers of Systemic Activity and Compliance", Clinical Cancer Research, vol. 10, 6847-6854, Oct. 15, 2004.
Sharma et al., "Curcumin: the story so far", Eur J of Cancer, 2005, 41:1955-68.
Sharma et al., "Pharmacokinetics and pharmacodynamics of curcumin", Adv Exp Med Biol., 2007, 595:453-70.
Sharma, et al., "Pharmacodynamic and pharmacokinetic study of oral curcuma extract in patients with colorectal cancer", Clin Cancer Res., 2001, 7:1894-1900.
Slaughter et al., "'Field cancerization' in oral stratified squamous epithelium", Cancer, 1953, 6:963-68.
Vareed et al., "Pharmacokinetics of curcumin conjugate metabolites in healthy human subjects", Cancer Epidemiol Biomarkers Prev., 2008, 17(6):1411-7.
Clark et al., "Curcumin Inhibits Carcinogen and Nicotine-Induced Mammalian Target of Rapamycin Pathway Activation in Head and Neck Squamous Cell Carcinoma", Cancer Prevention Research, 2010, 3(12):1586-1595.
PCT International Search Report and Written Opinion for Application No. PCT/US2015/052726 dated Feb. 19, 2016.
Sabinsa Product List Jan. 2008.
Wang et al., "Stability of curcumin in buffer solutions and characterization of its degradation products", Journal of Pharmaceutical and Biomedical Analysis, 1997, 15:1867-1876.
He et al., "Upregulation of p53 Expression in Patients with Colorectal Cancer by Administration of Curcumin", Cancer Investigation, 2011, 29:208-213.
Latimer et al., "Enhanced Systemic Bioavailability of Curcumin Through Transmucosal Administration of a Novel Microgranular Formulation", Anticancer Research, 2015, 35:6411-6418.
Panahi et al., "Effects of curcumin on serum cytokine concentrations in subjects with metabolic syndrome: A post-hoc analysis of a randomized controlled trial", Biomedicine & Pharmacotherapy, Aug. 2016, 82:578-582.
Usharani et al., "Effect of NCB-02, atorvastatin and placebo on endothelial function, oxidative stress and inflammatory markers in patients with type 2 diabetes mellitus: a randomized, parallel-group, placebo-controlled, 8-week study", Drugs R D, 2008, 9(4):243-250.

* cited by examiner

CONTINUOUS LOCAL SLOW-RELEASE OF THERAPEUTICS FOR HEAD AND NECK PROBLEMS AND UPPER AERODIGESTIVE DISORDERS

CROSS-REFERENCE TO RELATED APPLICATION

This application is a continuation application of U.S. application Ser. No. 12/544,997, filed Aug. 20, 2009, now abandoned; which claims the benefit under 35 U.S.C. 119(e) of U.S. Provisional Application No. 61/189,563, filed Aug. 20, 2008, which are incorporated by reference in their entirety herein.

BACKGROUND OF THE INVENTION

Field of the Invention

This invention relates to novel therapeutic formulations, their preparation, and methods of use for treating head, neck, and upper aerodigestive disorders.

State of the Art

Annually there are ~40,000 new head and neck squamous cell cancers (HNSCC) patients and 13,000 deaths in the US and 500,000 new cases worldwide (SEER 2007) Despite advances in treatment, the overall survival rates (~45%) have not improved significantly over the last three decades. Treatment failure in early stage disease is a result of second primary tumors (SPT) and, in advanced stage disease development, of local recurrence and metastasis resulting in morbidity and mortality. As a result of field cancerization, the probability of SPT occurs at a constant risk of 4-7% per year following initial treatment but can be as high as 22% within 5 years with a 5-year survival rate of 25% in these patients. Hence there is a need for chemopreventive agents to delay, arrest or reverse carcinogenesis. The entire mucosa exposed to the carcinogens in tobacco and alcohol have often undergone atypical changes. Moderate to severe dysplasia of the oral cavity and larynx is associated with a well-defined risk of progressing to invasive cancer in 33%-44% of patients. Hence, chemoprevention agents can be used as adjuvant therapy to prevent recurrences in HNSCC which occur in 2-3 years. One agent which appears to have promising potential in prevention of tumor progression is curcumin. Curcumin has been proposed as a chemoprevention agent but has poor bioavailability. Problems with dysphagia or difficulty swallowing occur from the cancer itself and from resection, mucositis, and xerostomia following chemotherapy and/or radiation therapy making it difficult for patients to swallow large pills which would be the case with curcumin as large doses are needed to overcome poor bioavailability.

Lessons Learned from Previous Studies and the Need for a Novel Agent:

Although preclinical studies have shown >1,000 compounds have chemopreventive properties, very few have made it to clinical trials. Retinoids are the best-studied class with five randomized retinoid trials conducted to date in premalignant oral lesions, that were shown to prevent recurrence and SPT. Although the trials showed significant response rates, dose related mucocutaneous toxicity has been the major adverse effect encountered in these trials. High relapse rates were also noted which indicates the need for prolonged maintenance therapy. In trials with retinoids for HNSCC patients, although SPTs were significantly reduced, there was no change in survival believed to be due to high toxicity-related drop out in the retinoid arm, highlighting the importance of thoroughly investigating dietary supplements such as curcumin for efficacy.

Improvement of Toxicity:

Non-steroidal anti-inflammatory drugs (NSAIDs) have also been widely investigated as chemoprevention agents, due to the anti-angiogenic properties of these agents in rodent models. A large study on the chemopreventive effects of the COX-2 inhibitor Celebrex® was halted because of increased risk of cardiovascular events and toxicities in patients. The COX-2 inhibitor Vioxx® is now removed from the market and the use of the other COX-2 inhibitor, Celebrex®, is markedly limited. There is a focus now to induce tumor cell apoptosis while compensating for COX function to increase efficacy and minimize toxicity. Given the need for a safer agent and the long term use of chemopreventive agents, curcumin has attracted attention due to its antitumor activity and negligible toxicity in humans and animals.

Curcumin and its Current Problems:

A natural product isolated from turmeric, curcumin has been implicated as a powerful therapeutic in a variety of human cancers because of its ability to induce apoptosis and is currently undergoing clinical trials for colon, skin, pancreatic, and hematologic cancers, although its effect on HNSCC has been limited for in vivo benefit due to low gastrointestinal absorption. Studies have shown increased bioavailability of curcumin when administered in conjunction with the black pepper extract piperine in both rats and humans (2000% in humans with a single dose), although the efficacy remains controversial. The commercially available combination of curcumin and piperine, Curcumin C3 Complex® (Sabinsa Corp. Piscataway, N.J.), is currently being evaluated in a phase III trial of metastatic colon cancer, with no dose-limiting toxicity reported in human clinical trials of curcumin up to 10 g/day.

Pharmacologically active levels of curcumin can be achieved in colorectal tissue in patients taking oral curcumin due to prolonged local contact. Although data is lacking, it is unlikely that pharmacologically active concentrations of curcumin can be achieved in tissues that are not directly exposed to a local application. Pharmacokinetic studies of curcumin indicate low bioavailability of curcumin following oral administration. There has been significant controversy with regards to Bioperine® and its role in improving the bioavailability of curcumin. Toxic side effects are inevitable for chemotherapy regimens, but are unacceptable for chemoprevention. Daily dosing of curcumin up to 8 grams daily for four months demonstrated no dose-limiting toxicity, although higher dosing was prohibited due to bulkiness of pills, which would pose a serious problem to head and neck cancer patients post-surgery or during radiation when swallowing is often impaired.

SUMMARY OF THE INVENTION

The invention features solid formulations and methods for the local and sustained slow-release delivery of therapies in the oral cavity for the treatment of head and neck disorders or disorders of the upper aerodigestive track.

In one embodiment of the invention, formulations and methods for the administration of curcumin are provided. Curcumin's poor bioavailability and the relatively high concentrations required for efficacy have limited its use, both of which are issues that can be overcome by the use of the present invention. By delivering curcumin, or other therapeutic agents locally, systemic bioavailability is not an issue and local concentrations in the mucosa are likely to reach the therapeutically effective levels. In some aspects, the present invention addresses this problem by providing solid formulations and methods for the delivery of curcumin and other therapeutic agents by absorption through the oral mucosa.

In accordance with one embodiment, this invention provides a solid formulation in the form of a chewing gum to locally delivery curcumin. In another embodiment, provided are lozenges for local and prolonged delivery of curcumin.

In another embodiment, provided are solid formulations containing curcumin and other agents such as phytochemicals and/or vitamins and minerals.

These and other embodiments of the invention are further described in the text and claims that follow.

DETAILED DESCRIPTION OF THE INVENTION

In one embodiment, provided is a solid oral formulation comprising a therapeutically effective amount of curcumin and a pharmaceutically acceptable carrier for oral mucosal delivery of said curcumin.

Suitable oral solid formulations include those in the form of chewing gums, lozenges, and candies for administration of curcumin through the oral mucosa. Such solid formulations contain pharmaceutically acceptable carriers relevant for that particular form, and such carriers will be well known to one of skill in the art. The formulations may be chewed, sucked, or placed against the buccal cavity or administered sublingually. The solid formulations may be in any number of shapes. Non-limiting examples include flat sticks or formulations having circular, octagonal, or biconvex shapes.

Pharmaceutical acceptable carriers include ingredients such as buffers, flavorings, aroma agents, sweeteners, colorants, preservatives such as antioxidants, softeners, thickening agents, emulsifiers, glidants, lubricants, and mixtures thereof.

One or more buffers may be used to aid in absorption of curcumin through the oral mucosa. Preferred buffers are those capable of increasing saliva pH to about 7 to 12, to about 7 to 11, or to about 7 to 10 during administration. Suitable buffers include sodium carbonate, sodium bicarbonate, calcium carbonate, potassium carbonate, potassium bicarbonate, sodium potassium dibasic, sodium potassium tribasic, potassium phosphate dibasic, potassium phosphate tribasic, magnesium hydroxide, potassium hydroxide, aluminum hydroxide, and mixtures thereof. In some aspects, buffers comprise about 0.1 to about 10% or about 0.1 to about 5% of the solid formulation.

Flavorants and aroma agents include essential oils and natural and synthetic compounds that mimic the flavors and aromas of fruits. Flavorants include those having a lemon, orange, lime, spearmint, wintergreen, chocolate, cinnamon, vanilla, coffee, or menthol taste. Suitable flavorant amounts include formulations having from about 0.1 to 0.5% by weight of the flavorant.

Sweeteners may be natural or artificial sweeteners. Examples of sweeteners include sucrose, fructose, mannitol, sorbitol, xylitol, powdered sugar, granulated sugar, molasses, saccharin, acesulfame, aspartame, Nutrasweet, Splenda, and mixtures thereof. In some aspects, sweeteners comprise about 0.001 to about 5% or 10% by weight of the solid formulation. In another aspect the sweetener comprises 0.5% by weight of the formulation.

Suitable colorants include dyes, pigments, and natural food colors approved for use as food additives. In some aspects, the colorants comprise about 0.001% to about 0.05% by weight of the formulation.

The solid formulations may also contain oils and lubricants to aid in the preparation of the formulation, such as to prevent sticking to equipment and molds. In some aspects the oils comprise up to 1% by weight of the formulation.

The curcumin used in the formulations may be prepared synthetically or preferably is isolated from natural sources.

In one embodiment, provided is a chewing gum optionally having a coating layer, wherein said gum comprises gum base, corn syrup, citric acid, glycerin, and a therapeutically effective amount of curcumin and optionally a sweetener.

Processes for preparing gum coatings are well known in the art. The coatings aid in enhancing taste and/or product stability during storage. Suitable coatings include those having a sweetened candy coating.

Gum base is a non-nutritive masticatory substance. It is an inert and insoluble non-nutritive product used as a support for the edible and soluble portion of the chewing gum (sweetener, glucose, flavors etc). The general description "gum base" used on chewing gum products throughout the world is recognized by The Food Chemicals Codex and most national legislation. Gum base is produced through a blend of raw materials which can be categorized in five classes: 1) elastomers; 2) resins to act as binders and softeners; 3) plasticizers to render the elastomer soft to ensure thorough blending of the gum base; 4) fillers to contribute to the overall texture; and 5) antioxidants to prevent oxidation of the gum base and flavors during shelf life. Suitable gum bases include natural and synthetic gum bases. Synthetic gum bases may contain a mixture of elastomers, plasticizers, fillers, softeners, emulsifiers, and waxes. Examples of gum bases include agar, alginate, arabic gum, carob gum, carrageenan, ghatti gum, guar gum, karaya gum, pectin, tragacanth gum, locust beam gum, gellan gum, and xantham gum. The gum base may comprise 10 to 80% by weight of the chewing gum, excluding the weight of any coating layer.

In some embodiments, the amount of curcumin in each piece of gum is between 1 and 500 mg. In other aspects, the amount of curcumin is 350 mg.

In other embodiments the gum base is between 0.5 and 2 g. In other aspects, the amount of gum base is 1.1 g.

In one embodiment, the solid formulation contains sweeteners selected from the group consisting of powdered sugar, granulated sugar, molasses, aspartame, Nutrasweet, and Splenda. In one aspect, the solid formulation contains between 0 and 2 g of sweetener.

In another embodiment, provided is a chewing gum having between 0.05 and 0.5 mL corn syrup for each piece of chewing gum. In some aspects, the chewing gum has 0.18 mL of corn syrup.

In another embodiment, provided is a chewing gum having between 5 mg and 25 mg of citric acid. In some aspects, the chewing gum has 12 mg of citric acid.

In another embodiment, provided is a chewing gum having between 0.01 and 1 mL glycerin. In some aspects, the chewing gum has 0.03 mL of glycerin.

In one embodiment, provided is a method for folding therapies into a chewing gum which upon chewing will be slowly released in the oral cavity such that up to 350 mg of the therapeutic can be solubilized (or wet), levigated and folded into a single piece of gum.

In the foregoing method, other phytochemicals, including, but not limited to EGCG (green tea polyphenol epigallocatechin-3-gallate), resveratrol, piperine, genistein, lycopene, lutein, perillyl alcohol, alpha-carotene, saponins, terpeneol, terpene limonoids, hesperetin, silymarin, tangeretin, ferulic acid, sulforaphene, and capsaicin can also be folded into the chewing gum as can other nutritional substances, including, but not limited to vitamins such as vitamin B, vitamin C, vitamin D, and vitamin E and minerals such as iron, calcium and potassium, and other nutritional supplements.

In one aspect, up to 375 mg of curcumin and other phytochemical or nutritional supplement is folded into the chewing gum. In other aspects, the amount of phytochemical is between 1 and 500 mg or is 350 mg.

In another aspect of the invention, phytochemicals, including, but not limited to curcumin, EGCG, resveratrol, piperine, genistein, lycopene, lutein, perillyl alcohol, alpha-carotene, saponins, terpeneol, terpene limonoids, hesperetin, silymarin, tangeretin, ferulic acid, sulforaphene, and capsaicin can be delivered to the oral cavity in the form of a spray or paste, as can other nutritional substances, including, but not limited to vitamins, such as vitamin B, vitamin C, vitamin D, and vitamin E, minerals, such as iron, calcium and potassium, and other nutritional supplements.

In the foregoing method, the paste would consist of up to the maximally soluble amount of the phytochemical or nutritional substance (to make 100 gm):

| | |
|---|---|
| Polyox ® WSR-301 | 5 gm |
| Pectin USP | 2 gm |
| Xanthan Gum | 1 gm |
| Gelatin | 2 gm |
| Acacia NF | 2 gm |
| Carboxymethylcellulose (Medium Viscosity) | 4 gm |
| Vaseline (petroleum jelly) | 84 gm |

Said paste should remain in the oral cavity for at least 10 minutes.

In one embodiment, provided are lozenges containing between 500 and 800 mg of curcumin. The lozenge may also contain one or more sweeteners and contain one or more buffers to facilitate transmucosal curcumin absorption.

In one embodiment, curcumin is present in the solid formulation as a nano-particle. Such particles may be formed according to the general methods disclosed in U.S. Pat. No. 5,145,684. In an illustrative example, curcumin is pulverized to nanoparticles in the presence of a surface modifier.

In the another embodiment of this invention, other phytochemicals, including but not limited to, EGCG, resveratrol, piperine, genistein, lycopene, lutein, perillyl alcohol, alpha-carotene, saponins, terpeneol, terpene limonoids, hesperetin, silymarin, tangeretin, ferulic acid, sulforaphene, and capsaicin can be used in the foregoing compositions at therapeutically effective concentrations. The phytochemicals can be used alone or in combinations of two or more, such that the combination does not exceed 25-60% (w/w) by weight of the solid formulation.

In other embodiments, the solid formulations further comprise Polyox® WSR-301, Pectin USP, Xanthan Gum, Gelatin, Acacia NF, Carboxymethylcellulose (Medium Viscosity), Vaseline (petroleum jelly) and curcumin or another phytochemical.

In other embodiments, the solid formulations further comprise Methocel® 2% gel and optionally another phytochemical.

In some aspects, the amount of curcumin or of another phytochemical is from 1 mg to the maximally soluble amount of curcumin or other phytochemical.

In another aspect, the invention features the use of the foregoing composition(s) to treat head and neck cancers. The foregoing composition(s) can also be used to treat or prevent other problems of the head and neck and upper aerodigestive disorders.

In still another aspect of the invention, the foregoing compositions can be used as a prophylactic to deliver nutritional supplements. In one embodiment of the invention, vitamins and/or minerals can be folded into the chewing gum such that the daily requirement of the vitamins and/or minerals is achieved in a patient by chewing one or more pieces of gum each day.

By "chemopreventative" is meant a compound that is capable of preventing the growth or re-growth of a tumor.

By "chewing gum" is meant a sweetened and flavored preparation for chewing.

By "formulation" is meant adding the therapeutic or chemopreventive compound to an acceptable carrier to facilitate delivery of the compound.

By "local delivery" or "local application" is meant delivering a therapeutically effective amount of the drug at the site of the disease, problem or disorder.

By "nutritional intervention" is meant use of a dietary supplement for improving health and reducing the risk of chronic disease or condition.

By "patient" is meant a mammal such as a human.

By "phytochemical" is meant non-nutritive plant chemicals that have protective or disease preventive properties.

By "proliferative disease" is meant a disease that is caused by or results in inappropriately high levels of cell division, inappropriately low levels of apoptosis, or both. For example, cancers such as lymphoma, leukemia, melanoma, ovarian cancer, breast cancer, pancreatic cancer, bladder cancer, gastric cancer, salivary gland carcinoma, head and neck cancer and lung cancer are all examples of proliferative disease. A myeloproliferative disease is another example of a proliferative disease.

By "therapeutically effective amount" is meant an amount of a compound sufficient to produce a preventative, healing, curative, stabilizing, or ameliorative effect in the treatment of a condition, e.g., a proliferative disease.

By "treating" is meant the medical management of a subject, e.g. an animal or human, with the intent that a prevention, cure, stabilization, or amelioration of the symptoms or condition will result. This term includes active treatment, that is, treatment directed specifically toward improvement of the disorder; palliative treatment, that is, treatment designed for the relief of symptoms rather than the curing of the disorder; preventive treatment, that is, treatment directed to prevention of disorder; and supportive treatment, that is, treatment employed to supplement another specific therapy directed toward the improvement of the disorder. The term "treatment" also includes symptomatic treatment, that is, treatment directed toward constitutional symptoms of the disorder. "Treating" a condition with the compounds of the invention involves administering such a compound, alone or in combination and by any appropriate means, to an animal, cell, lysate or extract derived from a cell, or a molecule derived from a cell.

Head and neck cancer patients carry a higher risk of developing second primaries, regardless of their initial treatment modality. The occurrence of a subsequent lesion in the entire respiratory and upper aerodigestive tract (UADT) is an important factor for mortality in HNSCC. An agent that can be used to treat HNSCC could be used for other UADT malignancies such as lung and esophagus. For example, squamous cell carcinoma (SCC) is a serious problem due to a prevalence of oral tobacco use and alcohol consumption, especially in the minority population.

Previous studies evaluating the effect of curcumin on TPA-induced (12-0-tetradecanoylphorbol-13-acetate) tumor promotion on mouse skin demonstrated that topical application of 10 µmol curcumin twice weekly inhibited the number of tumors per mouse by 98% (Huang M, Smart R, et al., 1988; Inhibitory effect of curcumin, chlorogenic acid, caffeic acid, and ferulic acid on tumor promotion in mouse skin by 12-O-tetradecanoyphorbol-13-acetate; Cancer Res 48(21):5941-6). Although tumors that develop in the hamster cheek pouch do not histologically or grossly resemble human oral carcinoma, topical application of 10 µmol curcumin to the cheek pouch of hamsters reduced the number of DMBA-induced (7,12-dimethylbenz(a)anthracene) oral tumors by ~40% when 10 µmol curcumin was applied topically 3 times/week for 24 weeks (Li N, Chen X, et al. 2002; Inhibition of 7,12-dimethylbenz[a]anthracene (DMBA)-induced oral carcinogenesis in hamsters by tea and curcumin; Carcinogenesis 23(8):1307-13). In a more recent study (Li M, Zhang Z, et al. 2007; Curcumin, a dietary component, has anticancer, chemosensitization, and radiosensitization effects by down-regulating the MDM2 oncogene through the PI3K/mTOR/ETS2 pathway; Cancer Res 67(5):1988-96), when curcumin was given by p.o. gavage at doses of 5 mg/day, 5 days/week for 4 weeks to tumor-bearing nude mice, curcumin inhibited growth of prostate cancer xenograft by ~50%. To date, a variety of animal models have addressed the chemopreventive properties of curcumin in colon or skin cancer.

HNSCC Cell Lines Screened for Sensitivity to Curcumin

Figure 1:
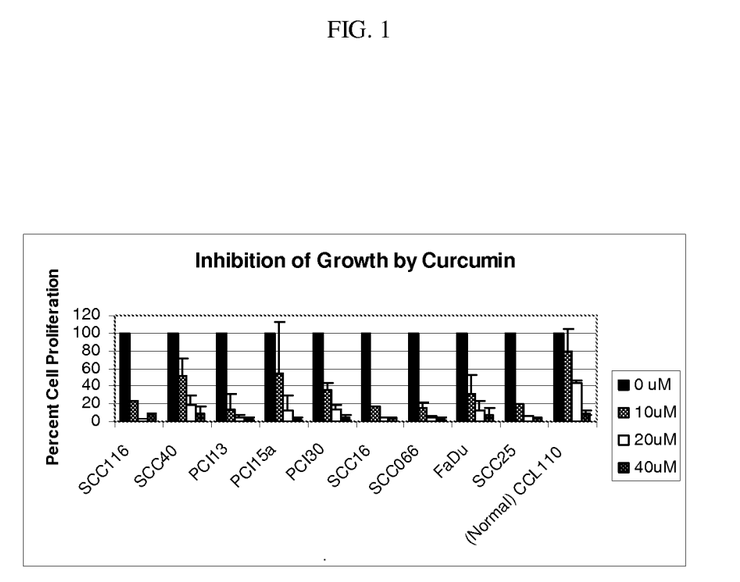
FIG. 1 represents the plot of growth inhibition of HNCC cells in vivo following treatment with the Curcumin C3 Complex®.

Our in vitro data with a variety of HNSCC cell lines has consistently demonstrated sensitivity of SCC cells to curcumin with consistent inhibition of cell proliferation at less than 10 µM curcumin while a higher dose of 20-40 µM was required to see effects in a normal fibroblast cell line CCL110 (FIG. 1). These results suggest the possibility of a favorable therapeutic window in vivo. It is striking that a variety of cell lines display a wide range of sensitivity to mTOR inhibitors, including rapamycin (sirolimus) and RAD001 (everolimus), whereas a variety of cell lines are consistently sensitive to curcumin within a narrow range at physiologically relevant concentrations.

Akt/mTOR Pathway is Activated in HNSCC and Margins Showing Precancerous Changes

Surgical excision of cancer with a curative intent is guided by obtaining histologically tumor-free margins. Most markers lack the sensitivity and ease of applicability for consistent clinical use. In a prospective study on surgical margins of HNSCC patients, we identified eIF4E as the first marker that is elevated in almost all tumor samples, which makes it a sensitive and readily detectable tumor marker in mucosal surgical margins. A total of 276 histologically tumor-free, mucosal surgical margins with a broad range of dysplasia (average of 4.25 margins per patient) from 65 patients were analyzed. Expression of eIF4E has also been shown to correlate with progressive cell transformation in the process of tumorigenesis. We further evaluated the potential of eIF4E downstream of the mTOR pathway as a biomarker by evaluating its expression in the oral cavity where chronic inflammation is a common occurrence. We then determined that over-expression of eIF4E in these margins is functionally active via activation of the Akt/mTOR pathway and also showed that molecular inhibitors of this pathway such as CCI-779, a rapamycin analogue, can inhibit tumor formation and improve survival in a model of minimal residual disease. This preferential activation of the Akt/mTOR pathway in our tumor-free margins compared with the tumor itself could be useful in the design of clinical trials with mTOR inhibitors, such as curcumin.

The Akt/mTOR Pathway as Biomarkers in Carcinogenesis

Figure 2:
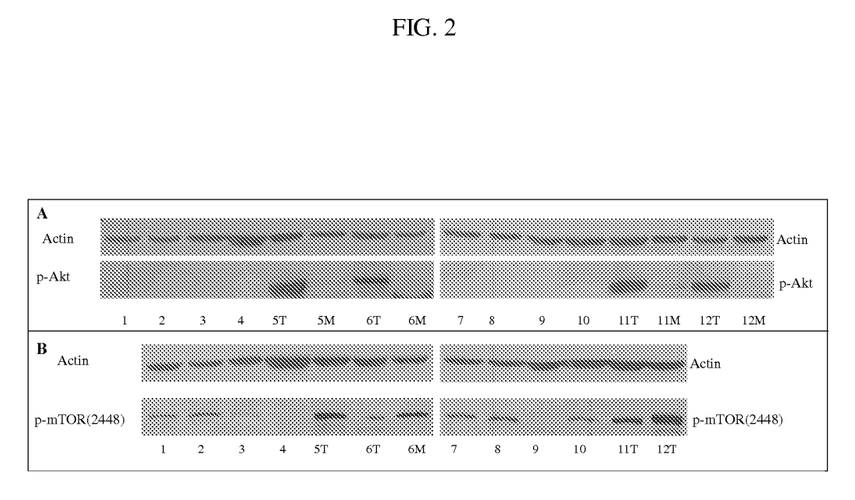
FIG. 2 is a western blot of tissue samples from sleep apnea non-cancer patients (1-4 and 7-10) and cancer patients (5, 6, 11, and 12) tumor (T) and histologically tumor-free margin (M) probed with antibodies against phospo-Akt (A) or phosphomTOR (B).

We have developed significant data to demonstrate that various parts of the Akt/mTOR pathway can serve as adequate biomarkers. Lippman proposed four criteria for biomarkers in tobacco related epithelial carcinogenesis and our data demonstrates that Akt/mTOR meet these requirements. Criteria #1) Biomarker expression in normal tissue should be different from that in high risk tissue. In FIG. 2 we present an analysis of cancer (lanes 5, 6, 11, and 12) and non-cancer (patients with sleep apnea) (lanes 1-4 and 7-10) patient samples. The cancer samples include tumors (T) and histologically tumor-free margins (M). No expression of pAkt was seen in mucosa of non-cancer patients while tumors and some margins express pAkt (FIG. 2). Similarly phospho-mTOR (p-mTOR) levels were significantly lower in non-cancer patients compared to cancer patients. Criteria #2) Biomarkers can be detected in small tissue specimens. In our studies we have successfully detected by western blots and even by IHC the various Akt/mTOR markers on samples often as small as 5 mm. Criteria #3) Biomarkers can be expressed in a quantity or pattern that can be correlated with the stage of carcinogenesis. We have successfully demonstrated such correlation in our study on precancerous tissue of the head and neck (Nathan C, Franklin S, et al. 1999; Expression of eIF4E during head and neck tumorigenesis: possible role in angiogenesis; Laryngoscope 109(8):1253-8). Criteria #4) Preclinical or early clinical data indicate that the condition represented by a marker can be modulated by study agents. We now also have exciting data indicating modulation of the mTOR pathway markers with an mTOR inhibitor not only in preclinical models but having completed our Phase 2 biomarker exploratory trial with temsirolimus (CCI-779), a rapamycin analogue, we show modulation of these markers in tumors and PBMCs (a potential surrogate marker) of HNSCC patients (Nathan C, Mills G, et al. 2007; An exploratory biomarker trial of an mTOR inhibitor in subjects with newly diagnosed advanced stage HNSCC; Proceedings AACR Supplement 48:42).

Mechanism of Antitumor Effects of Curcumin

A preliminary microarray analysis of gene expression profiles was used to characterize mechanisms of inhibition of cell proliferation in HNSCC exposed to 10 µM curcumin for 24-48 hours. Expression of many genes was modulated by curcumin, but two prominently affected pathways of interest were Akt/mTOR and NFκB. These results are the impetus to investigate in detail curcumin's effects on expression levels of genes in these two pathways.

Figure 3:
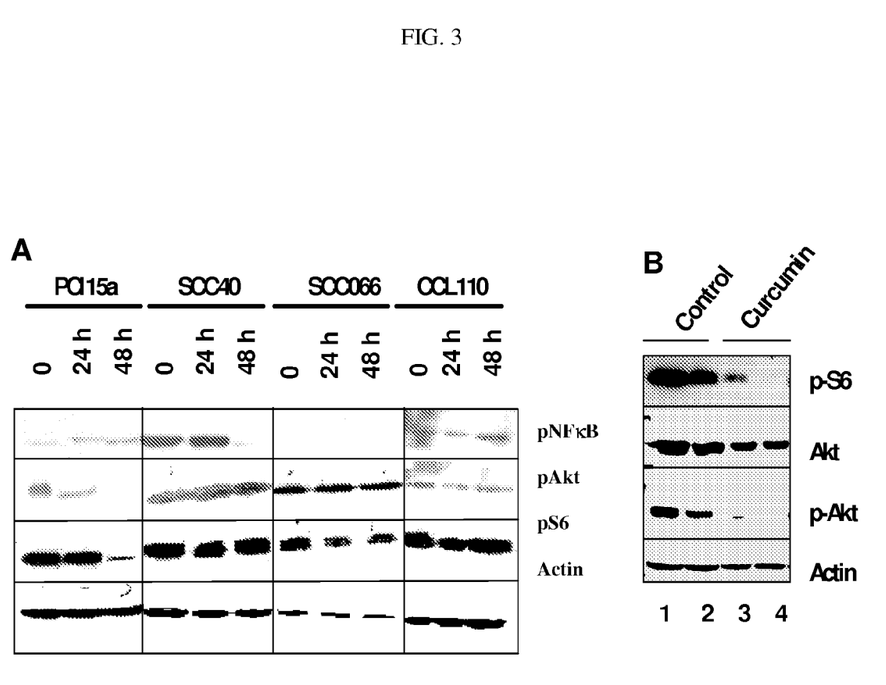
FIG. 3 represents curcumin's effects on NFκB and Akt/mTOR pathways in HNSCC cell lines in vitro (A) and in vivo (B).

The effects of curcumin on modulation of the NFκB and Akt/mTOR pathways were studied in 3 HNSCC and one normal fibroblast (CCL110) cell line after exposure to 10 µM of curcumin for 24 and 48 hours (FIG. 3A). Note all HNSCC cell lines showed inhibition of cell proliferation at 10 μM of curcumin (FIG. 1). Three HNSCC cell lines were treated with 10 μm curcumin for 24 and 48 hours and effects on the NFκB and Akt/mTOR pathway were analyzed. FIG. 3 shows that in PCI15a cells, although no change was noted in pNFκB, both pAkt and pS6 downstream of mTOR were down-regulated at 48 hours. On the contrary, SCC40 cells showed down-regulation of pNFκB after 48 hours and no change in the Akt/mTOR pathway. Finally SCC066 did not express pNFκB and did not show any modulation of the Akt/mTOR pathway. The normal fibroblast cell line CCL110 consistently showed no decrease in any of the pathways tested i.e. pNFκB or Akt/mTOR. It is interesting that although modulation of the biomarkers seems so variable in these cell lines all three HNSCC cell lines consistently showed significant growth inhibitory effects with curcumin at 48 hours. When mice with SCC40 xenografts were treated with curcumin there was a significant decrease in pAkt and pS6 (FIG. 3B Lanes 3 and 4) although this same cell line in vitro showed no decrease in the phosphorylation status of the Akt/mTOR pathway. The above data indicates: 1) a panel of biomarkers may be needed in nutritional intervention studies with curcumin as it appears to affect multiple pathways; 2) Although growth inhibitory in SCC40 cell culture, curcumin did not appear to down-regulate Akt/mTOR in cell culture, yet down-regulated the pathway in vivo. Hence the need for human clinical trials to validate biomarkers with nutritional intervention of safe compounds such as curcumin is important prior to embarking on large scale nutritional intervention studies with this bioactive food compound.

Given the above preliminary data it appears that although curcumin appears to have growth inhibitory effects on all 10 HNSCC cell lines tested to date, multiple pathways are inhibited. While curcumin can be used to treat these cancers, other compounds that act on these pathways may also be useful in treating these cancers and it should be readily recognized that such compounds could also be delivered by including in the formulations described herein.

Chemoprevention Model Updates

Balb/c nu/nu mice were randomized into treatment groups. In this set of experiments, we pre-treated mice with vehicle or higher doses of curcumin (10 or 15 mg) for 4 days prior to injecting tumor cells (Day 0). Tumors were measured over approximately three weeks. There was a statistically significant difference in tumor volumes between control (vehicle treated) and the 15 mg treated group of mice ($p=0.007$) by mixed [repeated] ANOVA analysis. However no significant difference was noted at 10 mg of curcumin indicating the importance that high doses may be required to overcome bioavailability. It was previously shown that curcumin has growth inhibitory effects in nude mice with established tumors and that the effects of curcumin were significant in the early stage of tumor development and not the later stages indicating curcumin's potential role as a chemopreventive agent or as adjuvant therapy to prevent recurrence. We show here the growth inhibitory effects of curcumin in the early stages of tumor development as expected with a cytostatic agent. This also points to its role as a chemopreventive agent rather than a therapeutic agent.

Accordingly, the invention provides methods of preventing and treating head and neck cancer using curcumin as a nutritional intervention or chemopreventative in patients following treatment of the primary tumor. Given the safety profile of curcumin and nutritional substances, such as vitamins, the solid formulations described can also be used as a prophylactic to prevent the occurrences of diseases or problems.

Formulations of Curcumin

Non-limiting illustrative examples of curcumin formulations are described below. In addition to the listed ingredients, any flavoring can be added.

In this example, spearmint oil is used as flavoring. To produce a piece of gum in a troche, the following ingredients are used:
Curcumin: 0.3 g
Gum Base: 1.098 gm
Powdered Sugar: 1.645 gm
Corn Syrup: 0.181 mL
Glycerin: 0.03 mL
Citric Acid USP monohydrate: 0.012 g The gum is prepared according to the following procedure:

1. Add gum base, citric acid, glycerin and corn syrup in a beaker. In a second beaker bring enough water to boil to allow a double boiler system. Melt the mixture of gum base ingredients until gooey. May use glass beadlet for bottom of second water beaker.

2. Measure amount of curcumin necessary to make required number of troches. Make a well to pour the melted gum base into on a clean pill tile.

3. Add flavor to the melted gum base and reheat if necessary to insure gooey texture. Pour the melted gum base into the center of the well of curcumin well and knead the two ingredients together using principles of geometric dilution.

4. Mix as fast as possible but with substantial kneading. Kneading too little will cause the gum to break up when chewed. Add to troche mold that is sprayed with Pam and standing by.

5. Remove from troche mold after about 20 minutes. May optionally dispense in a pill bottle.

Alternatively, it may be possible to use glycerin in step 2 and "wet" the curcumin to allow for increased dosage and better mixing.

The following is an example of a lozenge containing curcumin:
Curcumin: 0.3 g
Mannitol: 0.2 g
Xylitol: 1.3 g
Sodium carbonate: 0.5 g
Sodium bicarbonate: 0.15 g
Magnesium stearate: 0.01 g
Hydrogenated vegetable oil: 0.025 g The curcumin in dispersed in mannitol and the powders are mixed. The mixture is next compressed using a tablet press.

While the above examples describe the use of curcumin as the active ingredient, it should be obvious that any therapeutically effective compound, nutritional intervention or chemopreventative could also be formulated and delivered in a similar manner for the treatment of head and neck problems and upper aerodigestive disorders. Similarly, the above delivery strategies could be used to deliver nutrients, such as vitamins and minerals.

Synergistic Effects of Compounds with Other Compounds

While curcumin has been shown to be effective on its own in treating head and neck cancer and a variety of other disorders, phytochemicals or other therapies with different mechanisms of action, when combined with curcumin could result in even more robust effects. For example, curcumin is known to act on the Akt/mTOR pathway as described herein, whereas another phytochemical, EGCG, has been demonstrated to act at least in part on the c-met signaling pathway. Thus, the combination of these two compounds may result in more efficacious treatments. Similar, it should be readily apparent that other compounds acting on pathways outside the Akt/mTOR pathway could be combined and used as treatments in the formulations described herein.

Delivery of Nutrients

The formulations described in this invention, particularly the chewing gum, can also be used to delivery other nutrients, such as vitamins and minerals. While these are typically taken as one-a-day tablets or capsules, their incorporation and release from a chewing gum could increase compliance in children and some adults. A combination of vitamins and minerals could, therefore, be formulated in one or more pieces of gum such that the total would provide the FDA recommended daily allowance.

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

What is claimed is:

1. A method for treating head and neck cancers, said method comprising administering to a patient in need thereof a sustained slow-release chewing gum composition suitable for sublingual and/or oral transmucosal delivery of curcumin by absorption through the oral mucosa, said composition consisting of 350 mg to 800 mg of curcumin, gum base, corn syrup, citric acid and glycerin, wherein said curcumin is systemically bioavailable so as to provide therapeutic concentrations of curcumin in said patient.

2. The method of claim 1, wherein said head neck cancers are selected from the group consisting of head and neck squamous cell cancers and oral cavity squamous cell carcinoma.

3. The method of claim 1 wherein said curcumin is present in said composition as a nano-particle optionally in the presence of a surface modifier.

4. The method of claim 1 wherein said composition is administered in single or multiple doses.

5. The method of claim 1 wherein said composition optionally includes a coating layer.

6. The method of claim 1 wherein said composition comprises between 0.05 and 0.5 mL of corn syrup.

7. The method of claim 1 wherein said composition comprises between 5 mg and 25 mg of citric acid.

8. The method of claim 1 wherein said composition comprises between 0.01 and 1 mL of glycerin.

* * * * *